(12) United States Patent
Von Stein et al.

(10) Patent No.: US 7,569,352 B2
(45) Date of Patent: Aug. 4, 2009

(54) METHOD FOR IDENTIFYING MODULATORS OF THE DIOXIN/ARYL HYDROCARBON RECEPTOR (AHR)

(75) Inventors: Petra Von Stein, Spanga (SE); Patrik Andersson, Molndal (SE); Nikolai Kouznetsov, Jarfalla (RU); Lorenz Poellinger, Stockholm (SE)

(73) Assignee: InDex Pharmaceuticals AB, Stockholm (SE)

( * ) Notice: Subject to any disclaimer, the term of this patent is extended or adjusted under 35 U.S.C. 154(b) by 14 days.

(21) Appl. No.: 10/556,857

(22) PCT Filed: May 13, 2004

(86) PCT No.: PCT/SE2004/000748

§ 371 (c)(1),
(2), (4) Date: Oct. 20, 2006

(87) PCT Pub. No.: WO2004/102195

PCT Pub. Date: Nov. 25, 2004

(65) Prior Publication Data

US 2007/0042434 A1    Feb. 22, 2007

Related U.S. Application Data

(60) Provisional application No. 60/472,109, filed on May 21, 2003.

(30) Foreign Application Priority Data

May 14, 2003  (SE)  .................................. 0301395

(51) Int. Cl.
*G01N 33/52* (2006.01)
*G01N 33/567* (2006.01)
*C07H 21/04* (2006.01)

(52) U.S. Cl. ....................... 435/7.1; 435/7.21; 536/23.5

(58) Field of Classification Search ........................ None
See application file for complete search history.

(56) References Cited

U.S. PATENT DOCUMENTS 5,378,822 A * 1/1995 Bradfield et al. ........... 536/23.5

5,833,994 A * 11/1998 Wheelock et al. ........ 424/198.1

FOREIGN PATENT DOCUMENTS

WO    WO/02/34928    *  5/2002
WO    WO-02/34928 A1    5/2002

OTHER PUBLICATIONS

Al-Azzeh et al., Gastroprotective peptide trefoil factor family 2 gene is activated by upstream stimulating factor but not by c-Myc in gastrointestinal cancer cells. Gut, 51, 685-690, 2002.*
Wang et al, Transcriptional activation of cathepsin D gene expression by 17b-estradiol: mechanism of aryl hydrocarbon receptor-mediated inhibition. Mol.Cell. Endocrinol., 172, 91-103, 2001.*
Dossinger et al., Down-regulation of TFF expression in gastrointestinal cell lines by cytokines and nuclear factors. Cell Physiol. Biochem. 12, 197-206, 2002.*
May et al., Expression of Human Intestinal Trefoil Factor in Malignant Cells and its Regulation by Oestrogen in Breast Cancer Cells. J Patholo., 182, 404-413, 1997.*
Henley et al., Aryl hydrocarbon receptor-mediated post-transcriptional regulation of IL-1b. Arch. Biochem. Biophys., 422, 42-51, 2004.*
Ogata et al., Trefoil peptide expression and secretion is regulated by neuropeptides and acetylcholine. Am. J. Physiol., 273, G348-G354, 1997.*
International Search Report mailed Nov. 2, 2004, for PCT application No. PCT/SE2004/000748, filed May 13, 2004, 6 pages.
Kirikoshi, Hiroyuki et al. (2002) "Expression of TFF1, TFF2 and TFF3 in gastric cancer," International Journal of Oncology, 21: 655-659.

* cited by examiner

*Primary Examiner*—Lorraine Spector
*Assistant Examiner*—Elly-Gerald Stoica
(74) *Attorney, Agent, or Firm*—DLA Piper LLP (US)

(57) ABSTRACT

Agents useful for modulating the dioxin/aryl hydrocarbon receptor (AhR) can now be identified by determining the binding to said receptor and whether said agent suppresses or inhibits the expression of a gene substantially consisting of a sequence according to one of SEQ. ID. NO. 1 and SEQ. ID. NO. 2; a nucleotide sequence functionally homologous, or substantially homologous, or at least 90% identical to one of SEQ. ID. NO. 1 and SEQ. ID. NO. 2; and a nucleotide sequence complementary to the nucleotide sequence of SEQ. ID. NO. 1 or SEQ. ID. NO. 2. Such agents find utility in pharmaceutical compositions and methods for the prevention, alleviation or treatment of diseases involving gastrointestinal hyperplasia, such as gastrointestinal cancer or gastric cancer.

6 Claims, 5 Drawing Sheets

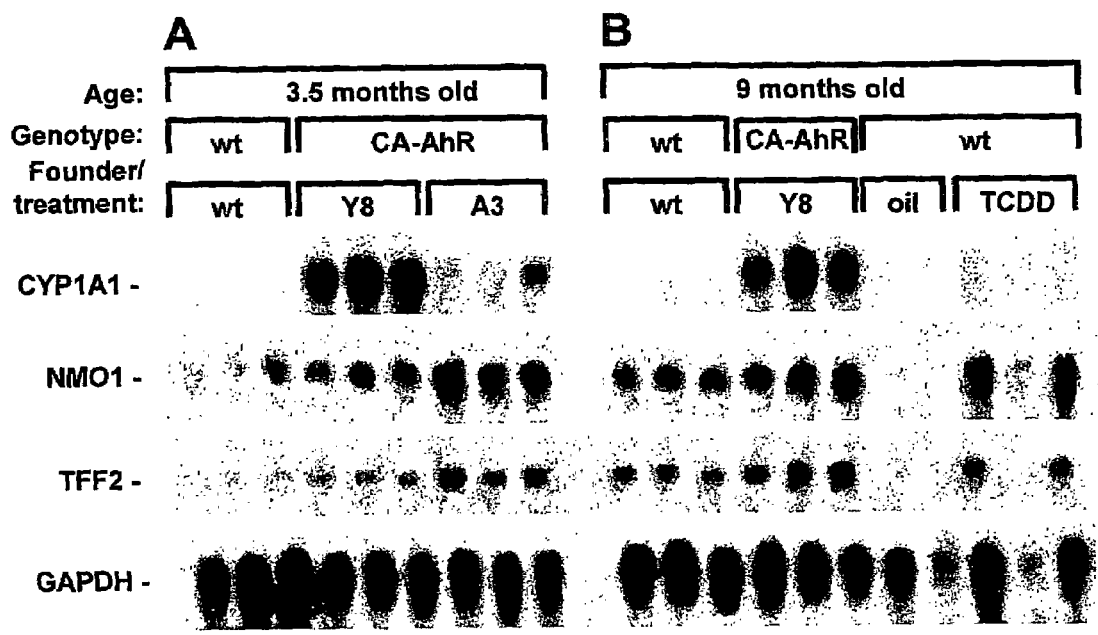
Fig. 2 A & B

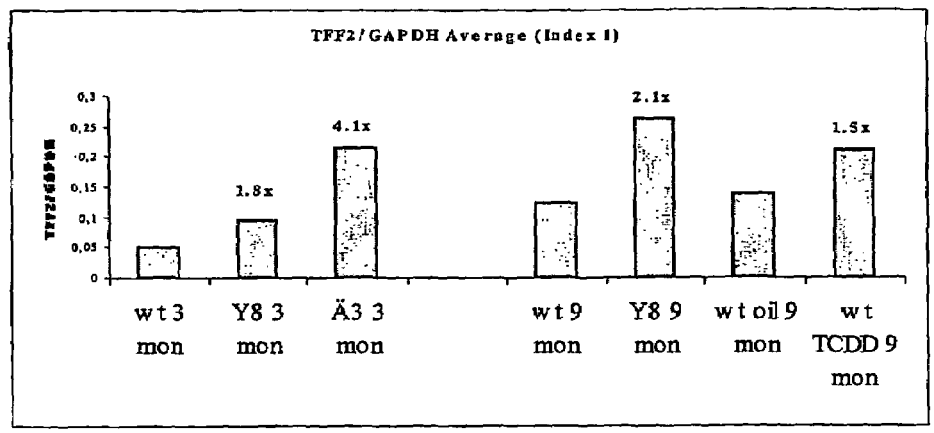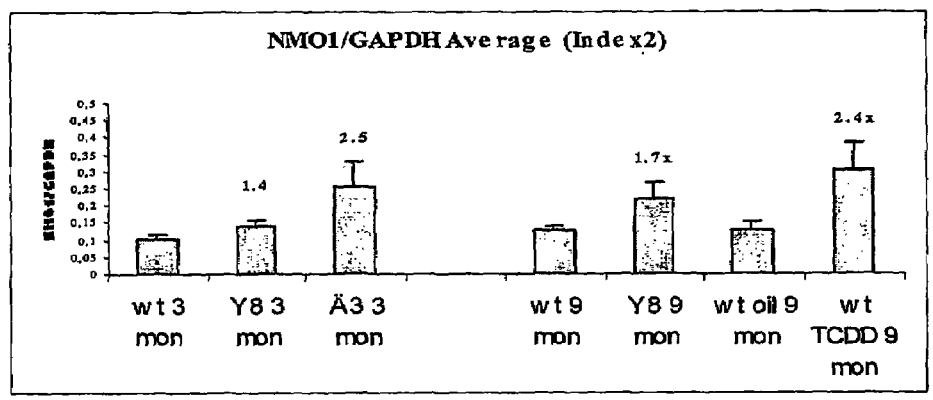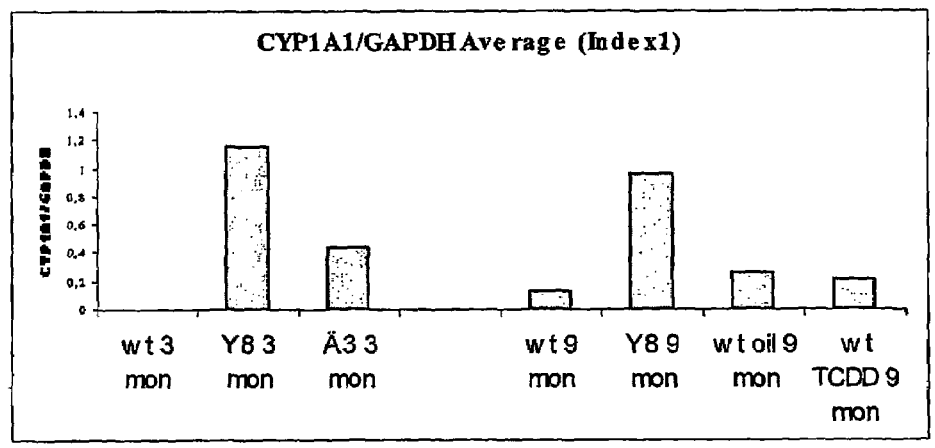
Fig.2 C, D & E

SEQUENCE LISTING

```
<160> NUMBER OF SEQ ID NOS: 2

<210> SEQ ID NO 1
<211> LENGTH: 389
<212> TYPE: DNA
<213> ORGANISM: Mus musculus

<400> SEQUENCE: 1
tgggccctcg aggtgcgccc ctgctggcag tggtcctggt tttgggactg catgctctgg      60
tagagggcga gaaaccttcc ccctgtcggt gctccaggct gacacccac aacagaaaga     120 actgtggctt cccgggcatc accagtgagc agtgctttga tcttggatgc tgctttgact     180
ctagcgtcgc tggggtccct tggtgtttcc acccacttcc aaaccaagaa tcggagcagt     240
gtgtcatgga agtgtcagct cgcaagaatt gtgggtaccc gggcatcagt cccgaggact     300
gtgccagtcg aaactgctgc ttttccaacc tgatctttga agtgccctgg tgtttcttcc     360
cacagtctgt ggaagattgt cactactga                                       389
```

```
<210> SEQ ID NO 2
<211> LENGTH: 390
<212> TYPE: DNA
<213> ORGANISM: Homo sapiens

<400> SEQUENCE: 2
atgggacggc gagacgccca gctcctggca gcgctcctcg tcctggggct atgtgccctg         60
gcggggagtg agaaaccctc cccctgccag tgctccaggc tgagccccca taacaggacg        120
aactgcggct tccctggaat caccagtgac cagtgttttg acaatggatg ctgtttcgac        180
tccagtgtca ctggggtccc ctggtgtttc caccccctcc caaagcaaga gtcggatcag        240
tgcgtcatgg aggtctcaga ccgaagaaac tgtggctacc cgggcatcag ccccgaggaa        300
tgcgcctctc ggaagtgctg cttctccaac ttcatctttg aagtgccctg gtgcttcttc        360
ccgaagtctg tggaagactg ccattactaa                                         390
```

US 7,569,352 B2

METHOD FOR IDENTIFYING MODULATORS OF THE DIOXIN/ARYL HYDROCARBON RECEPTOR (AHR)

CROSS REFERENCE TO RELATED APPLICATIONS

This application is a U.S. national phase application of International Application No. PCT/SE2004/000748, filed May 13, 2004, which claims priority to Swedish Application No. 0301395-0, filed May 14, 2003 and U.S. Provisional Patent Application Ser. No. 60/472,109 filed May 21, 2003, the contents of which are hereby incorporated by reference into the present disclosure in their entirety.

FIELD OF THE INVENTION

The present invention relates to changes in gene expression associated with the development of tumours in mammals, in particular gastrointestinal tumours. The invention provides methods for the identification of agents regulating trefoil factor 2 (TFF2) and the use of such agents for treatment of gastrointestinal tumours, as well as methods of such treatment.

BACKGROUND OF THE INVENTION

The Ah receptor belongs to a specific class of transcription factors, the basic helix-loop-helix/Per-Arnt-Sim domain (bHLH/PAS) proteins, which is emerging as a battery of regulatory factors seemingly designed to respond to environmental cues (Gu et al., 2000). The ligand-activated Ah receptor mediates transcriptional activation of a network of genes encoding drug metabolizing enzymes, e.g. CYP1A1, which function in the oxidative metabolism of xenobiotics (Pohjanvirta and Tuomisto, 1994). There exists a paucity of data on other target genes of the Ah receptor. In addition to genes encoding drug metabolizing enzymes, it has been reported that the Ah receptor directly or indirectly regulates the expression of the cell cycle regulator p27/kip1 in certain cells (Kolluri et al., 1999).

Transgenic mice expressing a constitutively active dioxin/aryl hydrocarbon receptor (CA-AhR) develop tumours of the glandular stomach from 3-4 months of age that correlate with increased mortality beginning at 6-9 months of age depending on founder line and sex of the animals (Andersson et al., 2002). Male CA-AhR mice develop more severe tumours than age-matched females. The tumours originate from the mucosa, penetrate through the muscularis mucosa and expand into the submucosa, muscularis propria and the subserosa. The well-studied target gene of the Ah receptor, CYP1A1, is expressed in many tissues of the CA-AhR mice also including the tumours, demonstrating transcriptional activity of the CA-AhR. However, neither CYP1A1 nor p27/kip1 have previously been implicated in the development of stomach tumours in humans or in experimental animals.

The tumours also show intestinal metaplasia. Exposure of experimental animals to Ah receptor ligands such as PCBs induce stomach tumours in rhesus monkeys (Allen and Norback, 1973; Becker et al., 1979) as well as intestinal metaplasia and adenocarcinoma of the glandular stomach in rat (Morgan et al., 1981). None of the target genes that to date have been described to be directly regulated by the Ah receptor can explain the phenotype observed in the stomach of the CA-AhR mice.

There is a constant need for new drugs and methods of treatment for the combat of cancer, as well as for new approaches for identifying substances for use in such drugs and methods. One problem underlying the present invention is how to find substances and methods for the prevention, alleviation, or treatment of gastrointestinal tumours.

SUMMARY OF THE INVENTION

The present invention is based on the discovery of TFF2 as being differentially expressed in tumours of the glandular stomach from transgenic mice expressing a constitutively active dioxin/aryl hydrocarbon receptor (CA-AhR). SEQ. ID. NO. 1 was identified and shown by the present inventors to be up-regulated in (CA-AhR) mice as a consequence of glandular tumour development, in particular stomach cancer. SEQ ID NO. 2 is the human equivalent of SEQ. ID. NO. 1.

Since TFF2 appears to be an important regulator of regeneration of gastric mucosa, increased expression of TFF2 may determine development of tumours in the CA-AhR mice. Taken together the present data strongly suggest that the Ah receptor regulates gastric expression of the TFF2 gene and thus may function as an important regulator of epithelial growth homeostasis in the stomach.

The present inventors therefore make available a method for identifying agents useful for modulating the dioxin/aryl hydrocarbon receptor (AhR), as well as agents useful in therapeutic applications for the prevention, alleviation, or treatment of gastrointestinal cancer, e.g. gastric cancer. The present invention also makes available such agents, characterized in their property of binding specifically to the dioxin/aryl hydrocarbon receptor (AhR) and suppressing or inhibiting the expression of a gene substantially consisting of a sequence according to one of (i) SEQ. ID. NO. 1 and SEQ. ID. NO. 2;
(ii) a nucleotide sequence substantially homologous to one of SEQ. ID. NO. 1 and SEQ. ID. NO. 2;
(iii) a nucleotide sequence at least 90% identical to one of SEQ. ID. NO. 1 and SEQ. ID. NO. 2; and
(iv) a nucleotide sequence complementary to the nucleotide sequence of SEQ. ID. NO. 1 or SEQ. ID. NO. 2.

The invention is further defined in the attached claims, incorporated herein by reference.

BRIEF DESCRIPTION OF THE DRAWINGS

The invention will be described in closer detail in the following description, examples, and attached drawings, in which

FIG. 2 demonstrates how the increased expression of TFF2 mRNA in the glandular stomach of the CA-AhR mice varies between transgenic founder lines and ages of the mice. This figure presents another RNA blot (30 µg total RNA) showing mRNA expression in the glandular stomach of CYP1A1, TFF2 and the housekeeping gene GAPDH. (A) mRNA expression in male mice (3.5 months old). The mice were wild-type (wt) and from two independent founder lines (Y8 and A3). (B) mRNA expression in male wild-type (wt) and CA-AhR (Y8) mice, 9 months old and mRNA expression in male wild-type (wt) mice treated with vehicle (oil) or TCDD (10 µg/kg body weight, per oral administration, 72 hours exposure). The band intensity of TFF2 (C), NMO1 (D) and CYP1A1 (E) was measured by Phosphor Imager analysis and normalized against expression of GAPDH. The bars represent average values (n=3 for all except wt oil, 9 months), and the error bars represent the corresponding standard deviations. The numbers represent the fold increase of CYP1A1 and TFF2 mRNA expression compared to the corresponding wild-type control.

Figure 1:
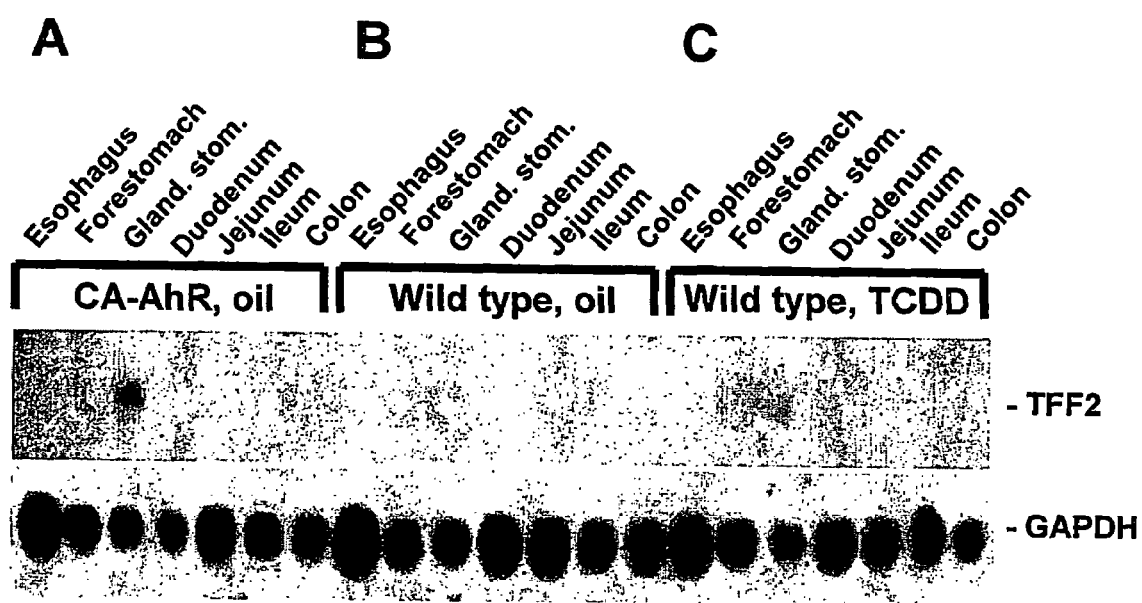
FIG. 1 shows the increased expression of TFF2 mRNA in forestomach and glandular stomach of the CA-AhR mice. The figure shows a RNA blot (2 µg poly-A RNA) showing mRNA expression of TFF2 and the house-keeping gene glyceraldehyde-3-phosphate dehydrogenase (GAPDH) in different parts of the gastrointestinal tract of 3 months old male CA-AhR (A) and age- and sex-matched wild-type animals treated with vehicle (B) or TCDD (C). Animals were treated per orally with TCDD in corn oil (10 µg/kg body weight) or corn oil only and organs were removed 24 hours later. The band intensity of TFF2 was measured by Phosphor Imager analysis and normalized against expression of GAPDH.
Figure 3:
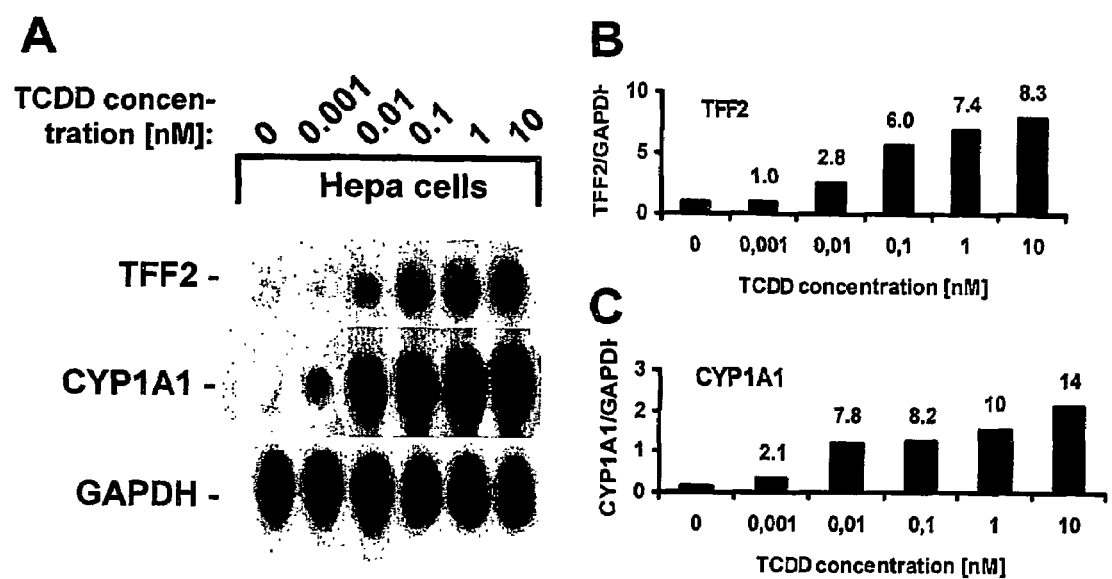

FIG. 3 shows a concentration-dependent increase of TFF2 and CYP1A1 mRNA expression in a mouse hepatoma cell line. (A) RNA blot (30 µg total RNA) showing mRNA expression in mouse hepatoma cells of TFF2, CYP1A1 and the housekeeping gene GAPDH after exposure to increasing concentrations of TCDD. Mouse hepatoma cells were cultured in 6 cm petri dishes and exposed to TCDD dissolved in dimethyl sulfoxid (DMSO, 0.1% total volume) at concentrations indicated in the figure, or vehicle alone ("0 nM") for 24 hours before cell harvest and RNA isolation. The band intensity of TFF2 (B) and CYP1A1 (C) was measured by Phosphor Imager analysis and normalized against expression of GAPDH. The numbers represent the fold increase of TFF2 and CYP1A1 mRNA expression compared to the corresponding vehicle-treated control.

Figure 4:
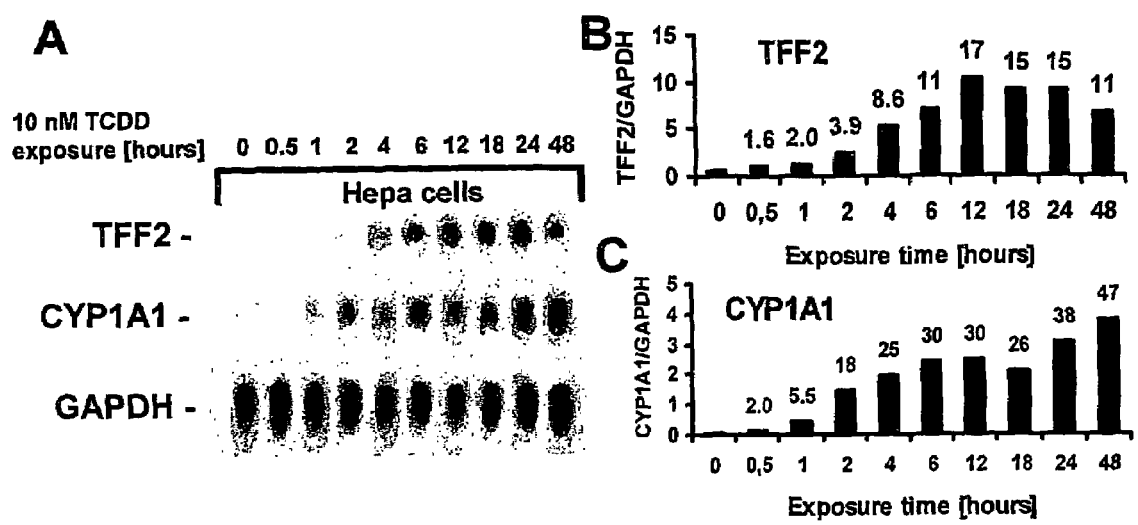

FIG. 4 shows the time-dependent increase of TFF2 and CYP1A1 mRNA expression in a mouse hepatoma cell line. (A) RNA blot (30 µg total RNA) showing mRNA expression in mouse hepatoma cells of TFF2, CYP1A1 and the housekeeping gene GAPDH after exposure to TCDD at increasing length of time. Mouse hepatoma cells were cultured in 6 cm petri dishes and exposed to 10 nM TCDD dissolved in dimethyl sulfoxid (DMSO, 0.1% total volume) for length of time indicated in the figure, or vehicle alone ("0 hours") for 48 hours before cell harvest and RNA isolation. The band intensity of TFF2 (B) and CYP1A1 (C) was measured by Phosphor Imager analysis and normalized against expression of GAPDH. The numbers represent the fold increase of TFF2 and CYP1A1 mRNA expression compared to the corresponding vehicle-treated control.

DESCRIPTION OF THE INVENTION

Before the present method is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

"Complementary" in the context of this description refers to the capacity for precise pairing between two nucleotides.

Further, in the context of the present invention, "hybridisation" refers to hydrogen bonding, which may be Watson-Crick, Hoogsteen or reverse Hoogsteen hydrogen bonding, between complementary nucleoside or nucleotide bases. Thus complementarity and hybridisation are terms used to indicate a sufficient degree of complementarity or precise paring such that stable and specific binding occurs between the oligonucleotide and the DNA or RNA target.

An antisense compound is specifically hybridisable when binding of the compound to the target DNA or RNA molecule interferes with the normal function of the target DNA or RNA to cause a loss of utility, and there is a sufficient degree of complementarity to avoid non-specific binding of the antisense compound to non-specific target sequences under conditions in which specific binding is desired.

The phrase "hybridisation under stringent conditions" refers to criteria regarding temperature and buffers well know to those skilled in the art.

Two DNA or polypeptide sequences are "substantially homologous" when at least about 75% (preferably at least about 80%, and more preferably at least about 90 or most preferably at least about 95%, or at least 96%, or at least 97% or at least 98% or at least 99%) of the nucleotides match over the defined length of the DNA sequences. Sequences that are substantially homologous can be identified by comparing the sequences using standard software available in sequence data banks, or in a Southern hybridisation experiment under, for example, stringent conditions as defined for that particular system. Defining appropriate hybridisation conditions is within the skill of the art.

"functionally homologous" means sequences sharing perhaps a lower structural homology with the disclosed sequence, but exhibiting homologous function in vivo, in either the healthy or the diseased organism, e.g. coding the same or highly similar proteins with similar cellular functions.

"Functionally inserted" or "operationally inserted" denotes that a sequence has been inserted in a host genome in such orientation, location and with such promoters, where applicable, that the correct expression of said sequence occurs.

"Modulation" as used in this context means either an increase (stimulation) or a decrease (inhibition) in the expression of a gene. In the context of the present invention, inhibition is the preferred form of modulation of gene expression and mRNA is a preferred target.

The phrase "pharmaceutically acceptable" refers to molecular entities and compositions that are physiologically tolerable and do not typically produce an allergic or similar untoward reaction, such as gastric upset, dizziness and the like, when administered to a patient.

The phrase "therapeutically effective amount" is used herein to mean an amount sufficient to suppress to some beneficial degree, preferably to reduce by at least about 30 percent, more preferably by at least 50 percent, most preferably by at least 90 percent, the development of tumours in mammals, in particular gastrointestinal tumours.

The present invention results from experiments performed in a proprietary transgenic animal model known as the CA-AhR mice (Index Pharmaceuticals AB, Stockholm, Sweden). The CA-AhR model is disclosed in WO 02/19813, incorporated herein by reference.

In an attempt to delineate which genes are dysregulated in the stomachs of the CA-AhR mice resulting in the stomach tumours, the present inventors performed gene expression profile analysis using a modified-version of subtractive hybridization analysis. Among the genes that were differentially regulated in the CA-AhR mice stomach, the results demonstrated increased expression of two previously known Ah receptor target genes but also a potential novel candidate gene contributing to tumour development, the trefoil factor 2 (TFF2).

In rat stomach, TFF2 is normally expressed in mucous neck cells as well as in the canaliculi of adjacent parietal cells (Hanby et al., 1999). This was also observed in the CA-AhR mice. TFF2 deficient mice show many effects of the stomach that appear to be the opposite phenotype of the CA-AhR mice, such as decreased proliferation and thickness of the mucosa as well as reduced number of mucous neck cells (Farrell et al., 2002), supporting the hypothesis that increased TFF2 expression may at least partly be involved in the stomach tumour development of the CA-AhR mice.

Consequently, the present invention makes available a method for identifying an agent useful for modulating the dioxin/aryl hydrocarbon receptor (AhR), said method comprising the steps of
(a) contacting a candidate agent with a mammalian AhR, and
(b) determining whether said candidate suppresses or inhibits the expression of a gene substantially consisting of a sequence according to one of
   (i) SEQ ID NO: 1 and SEQ ID NO: 2;
   (ii) a nucleotide sequence substantially homologous to one of SEQ. ID. NO. 1 and SEQ. ID. NO. 2;
   (iii) a nucleotide sequence at least 90% identical to one of SEQ. ID. NO. 1 and SEQ. ID. NO. 2; and
   (iv) a nucleotide sequence complementary to the nucleotide sequence of SEQ. ID. NO. 1 or SEQ. ID. NO. 2.
Preferably the sequence to be determined is one of
   (i) SEQ. ID. NO. 2;
   (ii) a nucleotide sequence substantially homologous to SEQ. ID. NO. 2;
   (iii) a nucleotide sequence at least 90% identical to SEQ. ID. NO. 2; and
   (iv) a nucleotide sequence complementary to SEQ. ID. NO. 2.
Most preferably the sequence to be determined is SEQ. ID. NO. 2 or a substantially homologous sequence.

The present invention also defines the use of an agent identified by the above method in the manufacture of a medicament for the treatment of gastrointestinal cancer or gastric cancer.

Further, the invention discloses a method for identifying an agent useful for the inhibition of tumour development in the gastrointestinal tract, said method comprising the steps
(a) contacting a candidate agent with a mammalian AhR, and
(b) determining whether said candidate suppresses or inhibits the expression of a gene substantially consisting of a sequence according to one of
   (i) SEQ ID NO: 1 and SEQ ID NO: 2;
   (ii) a nucleotide sequence substantially homologous to one of SEQ. ID. NO. 1 and SEQ. ID. NO. 2;
   (iii) a nucleotide sequence at least 90% identical to one of SEQ. ID. NO. 1 and SEQ. ID. NO. 2; and
   (iv) a nucleotide sequence complementary to the nucleotide sequence of SEQ. ID. NO. 1 or SEQ. ID. NO. 2.
such suppression or inhibition being indicative for an agent useful for the inhibition of tumour development.

Preferably, in the above method, the sequence to be determined is one of
   (i) SEQ. ID. NO. 2;
   (ii) a nucleotide sequence substantially homologous to SEQ. ID. NO. 2;
   (iii) a nucleotide sequence at least 90% identical to SEQ. ID. NO. 2; and
   (iv) a nucleotide sequence complementary to SEQ. ID. NO. 2.
Most preferably, the sequence to be determined is SEQ. ID. NO. 2 or a substantially homologous sequence.

The invention also encompasses the use of an agent or compound identified by the above method in the manufacture of a medicament for the treatment of gastrointestinal cancer or gastric cancer.

This agent or compound is administrated in a composition, containing the agent in a therapeutically effective amount, said composition formulated as occasioned by the intended mode of administration, and optionally combined with a suitable pharmaceutical carrier, optionally including adjuvants and excipients. Possible modes of administration include oral, enteral and rectal administration, local and systemic administration, such as intravenous administration. For oral administration, the compound is formulated as a tablet, capsule, caplet, lozange, effervacent tablet, controlled release tablet, enteral coated tablet. For enteral administration, the compound is formulated as an aqueous solution, a gel, a foam etc. For rectal administration, the compound is formulated as a suppository, an aqueous solution, a gel, a foam etc. For intravenous administration, the compound is formulated an injectable solution.

The medicament is formulated using conventional adjuvants, and the agents or compounds of the invention may thus be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Vehicles or compositions for delivery are well known to persons skilled in the art and can be applied to the delivery of the compound of the present invention, with or without minor modifications, without involving an inventive effort.

The agents regulating TFF2 according to the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The medicament optionally comprises one or more additional pharmacological agents for any of the disclosed therapeutic or prophylactic purposes.

Additionally, the invention makes available substances having the property of binding specifically to the dioxin/aryl hydrocarbon receptor (AhR) and inhibiting the expression of a gene substantially consisting of a sequence according to one of
   (i) SEQ ID NO: 1 and SEQ ID NO: 2;
   (ii) a nucleotide sequence substantially homologous to one of SEQ. ID. NO. 1 and SEQ. ID. NO. 2;
   (iii) (a nucleotide sequence at least 90% identical to one of SEQ ID NO: 1 and SEQ ID NO: 2; and
   (iv) a nucleotide sequence complementary to the nucleotide sequence of SEQ ID NO: 1 or SEQ ID NO: 2.

In general, the present invention discloses a method of regulating the function of trefoil factor 2 (TFF2) in a cell, a group of cells or an organism, comprising administering to said cell, group of cells or organism, a therapeutically effective amount of a compound which binds specifically to the dioxin/aryl hydrocarbon receptor (AhR) and inhibits the expression of a gene substantially consisting of a sequence according to one of
   (i) SEQ. ID. NO. 1 and SEQ. ID. NO. 2;
   (ii) a nucleotide sequence substantially homologous to one of SEQ. ID. NO. 1 and SEQ. ID. NO. 2;
   (iii) a nucleotide sequence functionally homologous to one of SEQ. ID. NO. 1 and SEQ. ID. NO. 2;
   (iv) (a nucleotide sequence at least 90% identical to one of SEQ. ID. NO. 1 and SEQ. ID. NO. 2; and
   (v) a nucleotide sequence complementary to the nucleotide sequence of SEQ. ID. NO. 1 or SEQ. ID. NO. 2.

Based on the above, the invention also entails methods for the treatment of a disease, preferably a disease involving gastrointestinal hyperplasia, such as gastrointestinal or gastric tumours, in a mammal, comprising administering a compound which binds to the aryl hydrocarbon receptor in an amount effective to suppress the expression of a gene substantially consisting of a sequence according to one of
(i) SEQ. ID. NO. 1 and SEQ. ID. NO. 2;
(ii) a nucleotide sequence substantially homologous to one of SEQ. ID. NO. 1 and SEQ. ID. NO. 2;
(iii) a nucleotide sequence functionally homologous to one of SEQ. ID. NO. 1 and SEQ. ID. NO. 2;
(iv) a nucleotide sequence at least 90% identical to one of SEQ. ID. NO. 1 and SEQ. ID. NO. 2; and
(v) a nucleotide sequence complementary to the nucleotide sequence of SEQ. ID. NO. 1 or SEQ. ID. NO. 2.

According to the invention, a compound capable of binding to the aryl hydrocarbon receptor (AhR) and capable of inhibiting or suppressing the expression of a gene as defined above, is administered to said mammal in a pharmaceutically acceptable and therapeutically effective dose, said dose being effective to suppress the expression of said gene.

The compound is administered in a composition, said composition formulated as occasioned by the intended mode of administration, and optionally combined with a suitable pharmaceutical carrier, optionally including adjuvants and excipients. Possible modes of administration include oral, enteral and rectal administration, local and systemic administration, such as intravenous administration. For oral administration, the compound is formulated as a tablet, capsule, caplet, lozenge, effervescent tablet, controlled release tablet, or an enteral coated tablet. For enteral administration, the compound is formulated as an aqueous solution, a gel, a foam etc. For rectal administration, the compound is formulated as a suppository, an aqueous solution, a gel, a foam etc. For intravenous administration, the compound is formulated an injectable solution.

Further embodiments of the invention will become apparent to a skilled person upon study of the examples.

EXAMPLES

1. Materials and Methods 1.1 Animals

CA-AhR animals were produced by pronuclear injection and bred to homozygosity (Andersson et al. 2002, see also Tallone et al., WO 02/19813). Transgenic and wild type control animals were of the same mixed genetic background. The animals were kept in ventilated filter top cages, were exposed to a 12 hour light/dark cycle and received water and standard rodent feed (RM3, Special Diet Services, Essex, UK) ad libitum. Age-matched wild type and CA-AhR mice were treated orally with corn oil or various doses of TCDD dissolved in corn oil as indicated in figure legends. Animals were sacrificed by $CO_2$ asphyxiation followed by cervical dislocation. Approval for all animal procedures was obtained from the local ethical committee on animal experiments.

1.2 Cell Culture

Gastric epithelial cell lines or mouse hepatoma 1c1c7 cells were cultured in minimal essential medium at 37° C. and 21% $O_2$. Exposure to TCDD or vehicle (DMSO) was done according to figure legends.

1.3 RNA Analysis

The glandular part of mouse stomachs was removed and snap-frozen in liquid nitrogen. Total RNA was prepared by tissue homogenization or cell lysis in a guanidinium thiocyanate buffer followed by CsCl2-gradient centrifugation (Sambrook et al., 1989). Poly-(A) RNA was isolated from total RNA using oligo-(dT)-coupled magnetic beads (Dynal Biotech, Oslo). The RNA was used for subtractive hybridization, or gene expression analysis by RT-PCR (please see below) or RNA blot analysis. RNA blot analysis was performed by standard methods. The filters were hybridized with specific 32P-labeled cDNA fragments and exposed to autoradiographic film and band intensity was quantified by Phosphoimager analysis (Fuji).

1.4 Subtractive Hybridization Analysis

The different steps of the subtractive hybridization analysis are described in detail below:

1.4.1 cDNA Synthesis 1.4.1.1 1-st Strand cDNA Synthesis

For first strand cDNA synthesis 2 g of RNA, 1 μl of 10 mM dNTPs (Gibco BRL), 1 μl of 10 μM Oligo-(dT)30-primer(5'-TTTTGTACAAGCTTTTTTTTTTTTTTTTTTTTT-TTTTTTTT-3') and twice distilled sterile water to final volume of 13 μl were mixed. The reactions were incubated for 5 min at 65° C. in a PCR machine (PCR SPRINT, Hybaid) and chilled on ice. Then, 4 μl of 5× first strand reaction buffer (Gibco BRL) and 2 μl of 100 mM DTT (Gibco BRL) were added and reactions were preheated to 42° C. Then, 1 μl of enzyme Superscript II RTase (Gibco BRL, 200 u/μl) was added and reactions were incubated for 1 h at 42° C. in a PCR machine.

1.4.1.2 2-nd Strand cDNA Synthesis

For second strand cDNA synthesis 32 μl of 5× second strand buffer (Gibco BRL), 3 μl of 10 mM dNTPs (Gibco BRL), 6 μl of 100 mM DTT (Gibco BRL), 93 μl bidistilled sterile water, 4 μl E.coli Polymerase I (New England Biolabs, 10 u/μl), 1.5 μl E.coli DNA Ligase (New England Biolabs, 10 u/μl), 0.7 μl RNAse H (Gibco BRL, 2 u/μl) were added to the reactions. The reactions were incubated for 2,5 hours at 16° C. in a PCR machine.

Fill-in reaction was performed by adding 5 μl of T4 DNA Polymerase (New England Biolabs, 3 u/μl) followed by 20 min incubation at 16° C. Full length cDNA was purified using Qiagen PCR Purification Kit according to the provided protocol. Samples were eluted with 35 μl of Elution buffer (10 mM tris-HCl, (pH8.5)) and 26 μl of each sample was used for the following steps.

1.4.2 Rsal Digestion of Full Length cDNA

Full-length double-stranded cDNA was incubated with 1 μl of restriction endonuclease Rsal (New England Biolabs, 10 u/μl) for 3 hours at 37° C. in 30 μl reaction containing 3 μl of 10× Rsal restriction buffer (New England Biolabs). Rsal-fragmented cDNA was purified using the Quiagen PCR Purification Kit and samples were eluted with 30 μl of Elution buffer.

1.4.3 Generation of Adapters

Double-stranded DNA adapter AD1 used for the subtraction procedure was generated by annealing of two complementary oligonucleotides:

```
AD1a
(5'-CTAATACGACTCACTATAGGGCTCGACCGGGCAGGCGGCCGCG
T-3')
and

AD1b
(5'-ACGCGGCCGCCT-3').
```

Double-stranded DNA adapter AD2 was generated by annealing of two complementary oligonucleotides:

AD2a
(5'-TGTAGCGTGAAGACGACAGAAAGGGCGGGAGGCCGTCGACCGT-3')
and

AD2b
(5'-ACGGTCGACGG-3').

Annealing was performed by incubation of oligonucleotide mixtures in Annealing buffer (150 mM NaCl, 10 mM tris-HCl (pH 8.0), 1 mM EDTA) in a preheated water bath (98° C.) followed by slow cooling down to room temperature.

1.4.4 Adaptor Ligation to Restricted cDNA

3 µl of restricted double-stranded cDNA (tester) were mixed with 2 µl of 100 pmol/µl AD1 or AD2 Adapter, 1 µl of 10× T4 DNA ligase buffer (New England Biolabs), 3 µl of twice distilled water and 1 µl of T4 DNA ligase (New England Biolabs, 2.000 u/µl). Ligation was performed by incubation at 16° C. (PCR SPRINT, Hybaid) for 8 hours.

1.4.5 Driver cDNA Preparation

The rest of purified Rsal-digested cDNA samples were lyophilized in a SpeedVac. Then, pellets were dissolved in 9 µl of twice distilled sterile water so that cDNA became 2× more concentrated in respect to tester cDNA.

1.4.6 Subtractive Hybridization

In order to subtract non-differentially expressed genes from differentially expressed ones, target cDNA (tester) was subtracted against an excess of control cDNA (driver). To identify genes which are up-regulated in target tissue of transgenic CA-AhR mice the tester cDNA was used as target cDNA (isolated from CA-AhR mice) and the control cDNA (isolated from WT mice) was used as driver. To identify genes, which are down-regulated, the control cDNA was used as tester and the target cDNA was used as driver. Two subtractions per mice (WT or transgene) were performed, in total—4 subtractions. Each subtraction was consisted of two sequential hybridization steps. Performed procedure is consistent with one described in PCR-Select cDNA Subtraction Kit (Clontech, Cat. No: 1804-1) with several variations.

1.4.6.1 1st Hybridization

For first hybridisation the driver cDNA was incubated with only one type of tester cDNA, that means two reactions per sample: 1 and 2 (Table 1). In Table 1 the pipetting scheme for the first hybridisabon step is described.

Using of adapters having complementary sequences on their ends, provide suppression of amplification of DNA template molecules with identical adapters ligated. This suppression occurs due to formation of intramolecular loop structure generated by annealing of complementary inverted terminal sequences of identical adapters as described in the prior art (See e.g. U.S. Pat. No. 5,565,340; Siebert et al., 1995; von Stein, Methods in Molecular Biology (2001), v.175, pp. 263-278).

TABLE 1

| Pipetting scheme | | |
|---|---|---|
|  | reaction 1 | reaction 2 |
| Driver | 1.5 µl | 1.5 µl |
| Tester (+AD1) | 1.5 µl | — |
| Tester (+AD2) | — | 1.5 µl |
| 4× hybridization buffer | 1.0 µl | 1.0 µl |
| mineral oil | 10 µl | 10 µl |

The reactions were pipeted in PCR tubes and incubated at 98° C. for 1.5 min and then at 68° C. for 8-9 hours.

1.4.6.2 2nd Hybridization

For the second hybridisation step, 0,5 µl of driver (target or control as before according to the subtraction), 0,5 µl of 4× Hybridization buffer (4 M NaCl, 200 mM HEPES (pH 8.3), 4 mM cetyltrimethyl ammonium bromide (CTAB)) 1 µl twice distilled sterile water were mixed and then reactions were overlayed with 6 µl of mineral oil.

The samples were incubated at 98° C. for 3 min and then the first hybridization reactions 1 and 2 were added to the reaction mixture. Then samples were incubated for 8 hours at 68° C. Hybridization reactions were diluted with 150 µl of Dilution buffer (20 mM HEPES-HCl (pH 8.3), 50 mM NaCl, 0.2 mM EDTA) followed by incubation for 10 min at 68° C.

1.4.7 PCR Amplification of Enriched Genes

After subtraction procedure the non-subtracted specific gene fragments were amplified using the ligated adaptors for priming the oligonucleotides. 2-step PCR amplification included primary (outer) PCR and secondary (inner) PCR.

1.4.7.1 Fill-in Reaction and Outer PCR Amplification

Outer PCR amplification was performed using two primers that anneal to the outer parts of adaptor sequences. Each PCR reaction contained 1 µl of diluted hybridization reaction mixed with 40 µl bidistilled water, 5 µl of 10 × Advantage PCR buffer (Clontech), 1 µl of 10 mM dNTPs mix, 1 µl of 10 µM primer P1 (5'-CTAATACGACTCACTATAGGGC-3'), 1 µl of 10 µM primer P2 (5'-TGTAGCGTGAAGACGACAGAAA-3'), 1 µl of 50× Advantage 2 Polimerase mix (Clontech). Polymerase reaction to fill-in missing strands of the adaptors was performed by initial incubation at 75° C. for 5 min in a PCR machine (PCR SPRINT, Hybaid). For outer PCR amplification the parameters were as following: 94° C. for 1 min and then 28 cycles: 94° C. for 20 sec, 66° C. for 30 sec and 72° C. for 2 min. PCR followed by incubation at 72° C. for 5 min in a PCR machine.

1.4.7.2 Inner PCR Amplification

The nested PCR amplification was performed using two primers that anneal to the inner parts of adaptor sequences. Each PCR reaction contained: 1 µl of 1:10 diluted outer PCR reaction mixed with 40 µl bidistilled water, 5 µl of 10× Advantage PCR buffer (Clontech), 1 µl of 10 mM dNTPs mix, 1 µl of 10 µM primer PN1 (5'-TCGACCGGGCAGGCGGC-CGCGT-3'), 1 µl of 10 µM primer PN2 (5'-AGGGCGGGAG-GCCGTCGACCGT-3'), 1 µl of 50× Advantage 2 Polimerase mix (Clontech).

The cycle parameters were: 94° C. for 1 min and then 18 cycles: 94° C. for 20 sec, 66° C. for 30 sec and 72° C. for 2 min. PCR was paused and aliquots (5 µl) were taken after 10, 12, 14, 16 and 18 cycles and visualized on 1× TAE 1.2% agarose gel. Minimal cycles number that gives a product that can be visualized by agarose gel electrophoresis was determined. Then inner PCR was performed with the same parameters for determined minimal number of cycles. Resulted PCR product was used for further cloning into a vector.

1.4.8 Evaluation of Subtraction Efficiency

Subtraction efficiency was evaluated by monitoring of expression of a number of genes that are known to show no differential expression (housekeeping genes: glyceraldehyde-3-phosphate dehydrogenase (GAPDH) and alpha-actin) and genes that expected to show differential expression in CA-AhR mouse model system (positively regulated AhR target gene: cytochrome CYP1A1).

1.4.9 SalI and NotI Digestion of Enriched cDNA

Amplified subtracted cDNA was sequentially digested with restriction endonucleases SalI (New England Biolabs, 20 u/µl and NotI (New England Biolabs, 10 u/µl) by incubation with 1 µl of restriction endonuclease for 3 hours at 37° C. in 30 µl, reaction containing 3 µl of 10× restriction buffer (New England Biolabs). Digested cDNA was purified using the Quiagen PCR Purification Kit and samples were eluted with 30 µl, of Elution buffer.

1.4.10 Ligation of the Enriched Differentially Expressed Genes into a Vector 6 µl of each amplified subtracted cDNA was used for the ligation into pSPORT1 vector (GIBCO Bri, pre-cut with SalI and NotI, 50 ng/µl). For that 2 µl of the vector and 1 µl T4 DNA ligase (New England Biolabs, 2.000 u/µl) were added and incubated for 5 hours at room temperature. 1 µl of each ligation sample (up and down) was transformed into 50 µl Chemomax efficiency DH5a competent cells (Gibco BRL) according to the manufacturers instructions.

1.4.11 Screening for the Differentially Expressed Genes

Clones number per µl of plated transformation mixture was estimated by counting of colonies on 1,5% agar LB plates containing 100 µg/ml ampicilin. Approximately 4000 clones from each subtraction were plated out on 22 cm square 1,5% agar LB plates containing 100 µg/ml ampicilin.

384 clones were picked from each of up- and down-subtracted libraries and innoculated in 384 well plates with 70 µl LB medium (100 µg/ml ampicilin) per well using BioPick machine of BioRobotics (Cambridge, UK). The cultures were incubated overnight at 37° C. and then used for colony PCR. This PCR was performed in 384 PCR plates in 20 µl volume per sample. Each PCR reaction contained: 2µl of 10× PCR buffer (100 mM tris-HCl (pH8.8), 500 mM KCl, 15 mM MgCl2), 0,4 µl of Sport-NotI primer (10 pmol/ml; 5'-CG-TAAGCTTGGATCCTCTAGAGC-3'), 0,4 ml of Sport-SalI primer (10 pmol/ml; 5'-TGCAGGTACCGGTCCGGAAT-TCC-3'), 1,6 µl of dNTP mixture (25 mM each), 0,4 µl of 0,1% Bromphenol Blue and 0,5 µl of DynAzyme Taq-polymerase (2U/ml; FynZyme). A master mixture for all reaction was prepared and distributed by multipipet device. The colony PCR cycle parameters were: 94° C. for 2 min followed by 37 cycles: 94° C. for 30 sec; 50° C. for 30 sec, 72° C. for 1 min. PCR followed by incubation at 72° C. for 5 min in a PCR machine.

1.4.12 Macroarray Filter Preparation

Resulted PCR products were spotted on Hybond N+ membrane (Amersham) using Microgrid TAS machine from BioRobotics (Cambridge, UK). All clones were spotted in duplicates and mouse genomic DNA was used as guide dots. On one filter all 384 up-regulated genes and all 384 down-regulated genes were positioned. From such a filter 12 duplicates were made for analyzing them by hybridization with different radioactive cDNA probes.

1.4.13 cDNA Probe Labeling

Up- and down-subtracted cDNAs were used for the labeling. For one probe 2 µl of the subtracted cDNA (25 ng) and 1 µl of each 10 µM primer PN1 and PN2 (10 pmol/ml) were added to 16 µl water, denatured for 3 min at 98° C. and chilled on ice. Then 5 µl of 10× Eco Polymerase buffer (New England Biolabs), 5 µl of dGTP/dTTP/dATP-mixture (each at 0,5 mM) and 13 µl of bidistilled sterile water were added. Finaly, 5 µl 33P-dCTP (Amersham) and 2 µl of DNA Polymerase I large fragment (Klenow exo-, 5 u/µl, New England Biolabs) was added, mixed and incubated at room temperature for 1 hour. Labeled probes were then purified using Probe QuantTM G-50 mini columns (Amersham) according to the manufacturer instructions. The efficiency of DNA probe labeling was checked by means of a radioactivity counter.

1.4.13 Hybridization Conditions

From the 12 spotted filters 4 filters were used for the hybridizations of the screening. The filters were pre-hybridized in 10 ml hybridization buffer (0.5 M phosphate buffer (pH 7.2), 1 mM EDTA, 7% SDS) for 4 hours at 65° C. in rotating hybridization oven (Hybaid) in hybridization cylinders. After 3 hours of pre-hybridization the hybridization buffer was exchanged with fresh 10 ml of buffer. Then the probes were denaturated for 3 min at 96° C., immediately chilled on ice, added to the hybridization cylinders containing filters and buffer and incubated for 12 hours at 65° C. in the rotating hybridization oven. Then filters were washed by following procedure: initially by a short rinse with wash solution I (40 mM phosphate buffer (pH7.2), 1 mM EDTA, 5% SDS), then twice at 65° C. for 15 min with wash solution I and then three times at 65° C. for 15 min with wash solution II (40 mM phosphate buffer (pH7.2), 1 mM EDTA, 1% SDS). Finally, filters were rinsed by 4×SSC buffer, dried out using Whatman 3MM paper and used for phosphoimager analysis.

1.4.14 Identification of the Differentially Expressed Genes

Further proceeding of autoradiogrammes was performed using Phosphoimager Fujifilm BAS 1800II with BAS 1800 III R program. The analysis of images was performed using appropriate software (ArrayVision version 6.0 from Imaging Research Inc., and Microsoft Excel). The resulting primary positive clones were analyzed by sequencing (MWG Biotech) followed by NCBI BLAST analysis.

The examples described above, as well as preliminary experiments indicate, that the inventive method for identifying agents useful for modulating the dioxin/aryl hydrocarbon receptor (AhR) is effective and would represent a short-cut to the development of new drugs for the prevention, alleviation, or treatment of gastrointestinal cancer. In the screening of substances, a reliable and fast in vitro test is of great value, as the accuracy of the first screening step is crucial for the economy and success of the remaining screening and validation program.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

REFERENCES

Al-azzeh, E. D., Fegert, P., Blin, N., and Gott, P. (2000). Transcription factor GATA-6 activates expression of gastroprotective trefoil genes TFF1 and TFF2. Biochim Biophys Acta 1490, 324-332.

Allen, J. R., and Norback, D. H. (1973). Polychlorinated biphenyl- and triphenyl-induced gastric mucosal hyperplasia in primates. Science 179, 498-499.

Becker, G. M., McNulty, W. P., and Bell, M. (1979). Polychlorinated biphenyl-induced morphologic changes in the gastric mucosa of the rhesus monkey. Lab Invest 40, 373-383.

Bulitta, C. J., Fleming, J. V., Raychowdhury, R., Taupin, D., Rosenberg, I., and Wang, T. C. (2002). Autoinduction of the trefoil factor 2 (TFF2) promoter requires an upstream cis-acting element. Biochem Biophys Res Commun 293, 366-374.

Chinery, R., and Playford, R. J. (1995). Combined intestinal trefoil factor and epidermal growth factor is prophylactic against indomethacin-induced gastric damage in the rat. Clin Sci (Lond) 88, 401-403.

Dignass, A., Lynch-Devaney, K., Kindon, H., Thim, L., and Podolsky, D. K. (1994). Trefoil peptides promote epithelial migration through a transforming growth factor beta-independent pathway. J Clin Invest 94, 376-383.

Farrell, J. J., Taupin, D., Koh, T. J., Chen, D., Zhao, C. M., Podolsky, D. K., and Wang, T. C. (2002). TFF2/SP-deficient mice show decreased gastric proliferation, increased acid secretion, and increased susceptibility to NSAID injury. J Clin Invest 109, 193-204.

Gu, Y. Z., Hogenesch, J. B., and Bradfield, C. A. (2000). The PAS superfamily: sensors of environmental and developmental signals. Annu Rev PharmacolToxicol 40, 519-561.

Hanby, A. M., Poulsom, R., Playford, R. J., and Wright, N. A. (1999). The mucous neck cell in the human gastric corpus: a distinctive, functional cell lineage. J Pathol 187, 331-337.

Kinoshita, K., Taupin, D. R., Itoh, H., and Podolsky, D. K. (2000). Distinct pathways of cell migration and antiapoptotic response to epithelial injury: structure-function analysis of human intestinal trefoil factor. Mol Cell Biol 20, 4680-4690.

Kolluri, S. K., Weiss, C., Koff, A., and Gottlicher, M. (1999). p27(Kip1) induction and inhibition of proliferation by the intracellular Ah receptor in developing thymus and hepatoma cells. Genes Dev 13, 1742-1753.

Lefebvre, O., Chenard, M. P., Masson, R., Linares, J., Dierich, A., LeMeur, M., Wendling, C., Tomasetto, C., Chambon, P., and Rio, M. C. (1996). Gastric mucosa abnormalities and tumourigenesis in mice lacking the pS2 trefoil protein [see comments]. Science 274, 259-262.

Lefebvre, O., Wolf, C., Kedinger, M., Chenard, M. P., Tomasetto, C., Chambon, P., and Rio, M. C. (1993). The mouse one P-domain (pS2) and two P-domain (mSP) genes exhibit distinct patterns of expression. J Cell Biol 122, 191-198.

Longman, R. J., Douthwaite, J., Sylvester, P. A., Poulsom, R., Corfield, A. P., Thomas, M. G., and Wright, N. A. (2000). Coordinated localisation of mucins and trefoil peptides in the ulcer associated cell lineage and the gastrointestinal mucosa. Gut 47, 792-800.

Mashimo, H., Wu, D. C., Podolsky, D. K., and Fishman, M. C. (1996). Impaired defense of intestinal mucosa in mice lacking intestinal trefoil factor. Science 274, 262-265.

Morgan, R. W., Ward, J. M., and Hartman, P. E. (1981). Aroclor 1254-induced intestinal metaplasia and adenocarcinoma in the glandular stomach of F344 rats. Cancer Res 41, 5052-5059.

Pohjanvirta, R., and Tuomisto, J. (1994). Short-term toxicity of 2,3,7,8-tetrachlorodibenzo-p-dioxin in laboratory animals: effects, mechanisms, and animal models. Pharmacol Rev 46, 483-549.

Ribieras, S., Lefebvre, O., Tomasetto, C., and Rio, M. C. (2001). Mouse Trefoil factor genes: genomic organization, sequences and methylation analyses. Gene 266, 67-75.

Sambrook, J., Fritsch, E. F., and Maniatis, T. (1989). Molecular cloning: A Laboratory Manual., 2 edn (Cold Spring Harbour, N.Y., Cold Spring Harbour Laboratory Press).

Taupin, D., Wu, D. C., Jeon, W. K., Devaney, K., Wang, T. C., and Podolsky, D. K. (1999). The trefoil gene family are coordinately expressed immediate-early genes: EGF receptor- and MAP kinase-dependent interregulation. J Clin Invest 103, R31-38.

Wang, T. C., Goldenring, J. R., Dangler, C., Ito, S., Mueller, A., Jeon, W. K., Koh, T. J., and Fox, J. G. (1998). Mice lacking secretory phospholipase A2 show altered apoptosis and differentiation with Helicobacter felis infection. Gastroenterology 114, 675-689.

Wright, N. A., Hoffmann, W., Otto, W. R., Rio, M. C., and Thim, L. (1997). Rolling in the clover: trefoil factor family (TFF)-domain peptides, cell migration and cancer. FEBS Lett 408, 121-123.

The invention claimed is:

1. A method for identifying an agent that modulates the dioxin/aryl hydrocarbon receptor (AhR), comprising:
   (a) contacting a candidate agent with a cell expressing mammalian AhR; and
   (b) determining whether the candidate agent suppresses or inhibits the expression of a gene expressed by the cell selected from SEQ ID NO:1 or SEQ ID NO:2;
   wherein suppression or inhibition of expression of SEQ ID NO:1 or SEQ ID NO:2 identifies the agent as a modulator of the dioxin/aryl hydrocarbon receptor (AhR).

2. The method according to claim 1, wherein the gene is SEQ ID NO:2.

3. A method for identifying an agent that modulates the dioxin/aryl hydrocarbon receptor (AhR) comprising:
   (a) contacting a candidate agent with a cell expressing mammalian AhR; and
   (b) determining whether the candidate agent suppresses or inhibits the expression of a gene expressed by the cell, wherein the gene is a nucleotide sequence at least 95% homologous to SEQ ID NO:1 or SEQ ID NO:2;
   wherein suppression or inhibition of expression of the gene identifies the agent as a modulator of the dioxin/aryl hydrocarbon receptor (AhR).

4. The method of claim 3, wherein the gene is a nucleotide sequence at least 95% homologous to SEQ ID NO:2.

5. A method for identifying an agent that modulates the dioxin/aryl hydrocarbon receptor (AhR) comprising:
   (a) contacting a candidate agent with a cell expressing mammalian AhR; and
   (b) determining whether the candidate agent suppresses or inhibits the expression of a gene expressed by the cell, wherein the gene is a nucleotide sequence at least 90% homologous to SEQ ID NO:1 or SEQ ID NO:2;
   wherein suppression or inhibition of expression of the gene identifies the agent as a modulator of the dioxin/aryl hydrocarbon receptor (AhR).

6. The method of claim 5, wherein the gene is a nucleotide sequence at least 90% homologous to SEQ ID NO:2.

* * * * *